United States Patent [19]

Köhler

[11] 4,239,550

[45] Dec. 16, 1980

[54] FLOWING AGENT FOR CONCRETE AND MORTAR AND PROCESS FOR PRODUCING THE SAME

[75] Inventor: Leo Köhler, Bobenheim, Fed. Rep. of Germany

[73] Assignee: Firma Holmen GmbH, Karlsruhe, Fed. Rep. of Germany

[21] Appl. No.: 6,812

[22] Filed: Jan. 26, 1979

[30] Foreign Application Priority Data

Jan. 30, 1978 [DE] Fed. Rep. of Germany ....... 2803923
Mar. 14, 1978 [DE] Fed. Rep. of Germany ....... 2811098

[51] Int. Cl.$^3$ ............................................... C04B 7/35
[52] U.S. Cl. ....................................... 106/314; 106/90
[58] Field of Search .............. 106/90, 314; 260/124 R

[56] References Cited

U.S. PATENT DOCUMENTS 3,686,119  8/1972  Markham et al. ............... 260/124 A

*Primary Examiner*—James Poer
*Attorney, Agent, or Firm*—Allison C. Collard; Thomas M. Galgano

[57] ABSTRACT

Flowing agent for concrete and mortar based, on the one hand, on lignin sulfonate and, on the other hand, on ring-sulfonated or sulfomethylated aromatic substances, wherein the mixture of the basic ingredients is after-condensed and after-sulfitized. The invention also relates to a process for making the flowing agent.

15 Claims, No Drawings

FLOWING AGENT FOR CONCRETE AND MORTAR AND PROCESS FOR PRODUCING THE SAME

The invention relates to a flowing agent for concrete and mortar based, on the one hand, on lignin sulfonate and, on the other hand, on ring-sulfonated or sulfomethylated aromatic compounds, as well as to a process for making the same.

Flowing agents serve the purpose of imparting to the concrete a high flowing capacity, on the one hand, without, on the other hand, increasing the setting times to an undesirable extent. It is known to liquefy concrete with lignin sulfonates and other dispersing agents. In the field of producing structural parts and in concrete for transportation or for reinforced concrete buildings, it has become a custom to use so-called super-liquefiers, in order to obtain an especially high flowing capability. For that purpose, lignin sulfonates have so far not proved to be useful. While for some other, limited sectors the good dispersion effect of lignin sulfonates at relatively low doses could be used without particular disadvantages, higher doses showed a better liquefaction, but resulted in the concrete's exuding and exhibiting undesirably long setting times.

Attempts have been made to utilize the high dispersion effect of lignin sulfonates by making a variety of mixtures with inorganic and organic salts (e.g., with dicarboxylic acids), in order to achieve better results. Since these attempts remained without success, synthetic dispersing agents were applied, derived from condensed aromatics, condensed heterocyclics, and amino compounds. With the use of these (last mentioned) agents, the setting times remained within desired limits, but the exudation sympton could not be entirely avoided. Moreover, these agents, while not being entirely satisfactory, were much too expensive when compared with pure lignin sulfonates or derivatives.

It is the object of the present invention to provide a flowing agent, based on lignin sulphonate, which is inexpensive and which fulfills the necessary requirements in the technology of concrete, as regards liquefaction, setting behavior, and dosage, while being particularly useful owing to its low price.

It is a further object of the invention to provide a process for manufacturing such a lignin sulfonate-based flowing agent in an advantageous manner.

These objects are accomplished, according to the invention, by subjecting the mixture of the basic ingredients mentioned in the beginning, to an after-condensation and after-sulfitation. A so produced flowing agent is inexpensive and yet comes fully up to the specifications of flowing capability and setting times and of the amount used to impart these properties.

The process for making this flowing agent for concrete and mortar based on lignin sulfonate, on the one hand, and ring-sulfonated aromatics or sulfomethylated aromatics, on the other hand, proceeds by subjecting an aromatic compound to sulfonation with sulfuric acid until clear water solubility appears, whereafter condensation is performed with urea and formaldehyde; then, according to a preferred mode of operation, lignin sulfonate is added to the condensate and with further addition of urea and formaldehyde, after-condensation takes place, and finally sodium sulfite added leads to after-sulfitation.

Another process for making the flowing agent for concrete and mortar according to the invention using lignin sulfonate and ring-substituted aromatics starts with an aromatic to which water and sodium sulfite is added for sulfitation, whereupon condensation with formaldehyde is performed; then lignin sulfonate is added and, after condensation with urea and formaldehyde, an after-sulfitation with sodium sulfite is carried out.

When the starting materials are limited to lignin sulfonate, on the one hand, and a ring-sulfonated aromatic, on the other hand, a further variant of the process for making the flowing agent according to the invention, proceeds by sulfonating an aromatic with addition of sulfuric acid to a time, when water solubility with formation of a clear product is obtained, whereupon condensation with urea and formaldehyde takes place, which causes the ring-substituted aromatic first to be after-sulfitated. The final condensation is made to occur by addition of lignin sulfonate, urea and formaldehyde.

For the purposes of the invention, fermented or unfermented lignin sulfonates may be used, but also lignin sulfonates, in which the sugar contained therein has been destroyed by alkaline oxidation.

The lignin liquor can contain as cation, calcium, magnesium, aluminum, sodium or ammonium, the cation exchange being brought about, before lignin sulfonate is added, by salt conversion.

The process according to the invention is carried out preferably at a pH-value of 4–8.

The flowing agent, according to the invention, imparts to concrete or mortar high fluidity, without leading to undesirable exuding or undesirably long setting times. Furthermore, the agent is much less expensive than other flowing agents, which as regards their advantageous properties would be closest to the one according to the invention; particularly the possibility of using a much higher amount of lignin sulfonate, while achieving at least the same results, is considered a remarkable economical advantage.

The invention will now be more fully described in a number of examples.

As ring-sulfonated aromatics, phenol, naphthalene, or cresol, or any desired mixture of these compounds may be used in the process of the invention.

A. Preparation of a flowing agent based on lignin sulfonate and ring-substituted aromatic.

The selected aromatic is sulfonated with sulfuric acid until clear water solubility is obtained; it is then condensed with urea and formaldehyde. After-condensation of the condensate is carried out by addition of lignin sulfonate, urea and formaldehyde, whereupon after-sulfitation takes place with sodium sulfite.

EXAMPLE 1

100 parts of phenol are sulfonated with 120 parts of conc. sulfuric acid at 115° C. for 2 hours in an autoclave, then the mass is cooled to about 50° C.;

Condensation: 30 parts urea / 70–80 parts water } 2 hours at 50° C.;

100 parts formaldehyde of 30% are added, continued to be condensed at 30°–50° C. for 12 hours;
add: 400–500 parts 45% lignin sulfonate, stir 30 minutes at 30°–80° C.;

add: 20–50 parts urea, stir 30 minutes at 30°–80° C.;

add: 50–100 parts 30% formaldehyde, stir 30 minutes at 30°–80° C.;

add: 30–60 parts sodium sulfite, stir 30 minutes at 30°–80° C.;

add: Water until desired dry substance is obtained; adjust pH to 4–8.

In this, as in all the following examples, parts are by weight. The selected aromatic is sulfonated with sulfuric acid until it is water soluble and clear, then condensation with urea and formaldehyde is carried out. According to one variant of the process, sulfitation then takes place with sodium sulfite, and subsequently after addition of lignin sulfonate after-condensation occurs with urea and formaldehyde.

EXAMPLE 2

100 parts of phenol are sulfonated with 120 parts sulfuric acid at 115° C. for 2 hours in an autoclave, then the mass is cooled to about 50° C.;

| Condensation: | 30 parts of urea | } 2 hours at 50° C.; |
|---|---|---|
| | 70–80 parts water | |

100 parts of 30% formaldehyde are added and condensation is continued for 12 hours at 30°–50° C.; then the mass is heated to 80° C. and 30–60 parts sodium sulfite is added for sulfitation for one hour; whereupon add: 100–300 parts 30% formaldehyde, stir 60 minutes at 50°–80° C.;

add: 400–800 parts 45% lignin sulfonate and stir 60 minutes at 50°–80° C.;

add: Water, until desired dry substance is obtained. pH 4–8 adjusted.

EXAMPLE 3

100 parts of phenol are sulfonated with 120 parts sulfuric acid at 115° C. for 2 hours in an autoclave, then the mass is cooled to about 50° C.;

| Condensation: | 30 parts urea | } 2 hours at 50° C.; |
|---|---|---|
| | 70–80 parts water | |

100 parts of 30% formaldehyde are added and condensation is continued for 12 hours at 30°–50° C.; then the mass is heated to 80° C. and 30–60 parts sodium sulfite is added for sulfitation for one hour; whereupon add: 400–800 parts 45% lignin sulfonate, stir 60 minutes at 50°–80° C.;

add: 100–300 parts 30% formaldehyde, stir 60 minutes at 50°–80° C.;

add: 20–50 parts urea, stir 60 minutes at 50°–80° C.; adjust pH to 4–8.

B. Preparation of a flowing agent based on lignin sulfonate and sulfomethylated aromatic The chosen aromatic is sulfitated with sodium sulfite and water; subsequently, condensation with formaldehyde takes place. Then, lignin sulfonate is added, after-condensed with urea and formaldehyde, and after-sulfitated with sodium sulfite.

EXAMPLE 4

100 parts of phenol, 40 parts of sodium sulfite, and 30 parts water are sulfitated for one hour at 100° C.; then follows the addition of 100 parts of 30% formaldehyde and condensation is carried out for 2.5 hours at 105° C.: After having distilled off 40 parts of water, the mass is cooled and diluted;

add: 200–300 parts lignin sulfonate of 45% and stir 30 minutes at 30°–80° C.;

add: 20–50 parts urea, and stir 30 minutes at about 30°–80° C.;

add: 50–100 parts formaldehyde of 30% and stir 30 minutes at 30°–80° C.;

add: 30–60 parts sodium sulfite, stir 30 minutes at 30°–80° C.;

add: Water until the desired dry substance is obtained. pH adjusted to 4–8.

The lignin sulfonate may be added in the process according to the invention as fermented or absolutely sugar-free liquor, which contains calcium, magnesium, aluminum, sodium or ammonium as cations.

I claim:

1. A flowing agent for concrete and mortar comprising a mixture of lignin sulfonate and sulfomethylated or ring-sulfonated aromatic compounds selected from the group consisting of phenol, napthalene, cresol and a mixture thereof, wherein said mixture is after-condensed and after-sulfitized.

2. A process for producing a flowing agent for concrete and mortar comprising the steps of:
sulfonating a ring-sulfonated or sulfomethylated aromatic compound with sulfuric acid until a clear water-soluble product is obtained;
condensing with urea and formaldehyde to obtain a condensate;
adding lignin sulfonate to said condensate;
adding urea and formaldehyde to effect after-condensation; and
adding sodium sulfite to effect after-sulfitation.

3. The process, according to claim 2 characterized by the use of fermented lignin sulfonate.

4. The process, according to claim 2 characterized by the use of unfermented lignin sulfonate.

5. The process, according to claim 2 characterized by destroying the sugar contained in the lignin sulfonate by alkaline oxidation, before the lignin sulfonate is added.

6. The process, according to claim 2 characterized thereby that the lignin sulfonate liquor contains as cation a member of the group consisting of calcium, magnesium, aluminum, sodium, and ammonium.

7. The process, according to claim 2 characterized thereby that the pH-value at which the process is carried out is adjusted to 4–8.

8. A process for producing a flowing agent for concrete and mortar comprising the steps of:
sulfitizing a ring-sulfonated or sulfomethylated aromatic compound with water and sodium sulfite;
adding formaldehyde to effect condensation;
adding lignin sulfonate;
after-condensing by adding urea and formaldehyde; and
adding sodium sulfite to effect after-sulfitation.

9. A process for producing a flowing agent for concrete and mortar comprising the steps of:
sulfonating a ring-substituted aromatic compound with sulfuric acid until a clear, water-soluble product is obtained;
condensing by adding urea and formaldehyde;
subjecting said ring-sulfonated aromatic compound to after-sulfitation with sodium sulfite;
adding formaldehyde to effect after-condensation;

adding lignin sulfonate; and subsequently adding urea for a final condensation.

10. The process according to claim 9, wherein said step of subjecting the ring-sulfonated aromatic compound to after-sulfitation is followed, in turn, by the steps of after-condensing with formaldehyde, adding lignin sulfonate, and finally treating with urea for final condensation.

11. The process according to claim 9, wherein said lignin sulfonate is added when the after-sulfitizing of the ring-substituted aromatic compound has taken place, which is then followed by after-condensing with formaldehyde and the final treatment step of adding urea for final condensation.

12. The process according to claim 2, wherein said sulfonating step comprises sulfonating 100 parts phenol with 120 parts of concentrated sulfuric acid at 115° C. for two hours in an autoclave and then cooling the resulting mass to 50° C., wherein said condensing step comprises condensing with 30 parts urea and 70-80 parts water for two hours at 50° C., then adding 100 parts 30% formaldehyde and continuing condensation for 12 hours at 30°-50° C., wherein said step of adding lignin sulfonate then takes place which comprises adding 400-500 parts of 45% lignin sulfonate followed by 30 minutes of stirring at 30°-80° C., wherein 50-100 parts of 30% formaldehyde is then added to effect after-condensation and is followed by 30 minutes of stirring at 30°-80° C. and wherein said process additionally includes the steps of adding water to obtain a desired degree of dryness in the final product and adjusting the pH to 4-8.

13. The process according to claim 10, wherein said sulfonating step comprises sulfonating 100 parts phenol with 120 parts conc. sulfuric acid at 115° C. for two hours in an autoclave, then cooling to 50° C., wherein said condensing step then takes place and comprises condensing with 30 parts urea and 70-80 parts water for two hours at 50° C., thereupon adding 100 parts 30% formaldehyde and continuing the condensation for 12 hours at 30°-50° C., wherein said step of subjecting said compound to after-sulfitation comprises subsequently heating up to 80° C. and after-sulfitizing for one hour with 30-60 parts sodium sulfite, wherein said after-condensing step comprises adding 100-300 parts 30% formaldehyde and stirring for 60 minutes at 50°-80° C., wherein said step of adding lignin sulfonate comprises adding 400-800 parts 45% lignin sulfonate and stirring for 60 minutes at 50°-80° C., wherein said step of adding urea comprises adding 20-50 parts urea and stirring for 60 minutes at 50°-80° C., and wherein said process additionally includes the steps of adding water to obtain a substance of desired dryness while adjusting the pH to 4-8.

14. The process according to claim 8, wherein said sulfitizing step comprises sulfitizing 100 parts phenol with 40 parts sodium sulfite and 30 parts water for one hour at 100° C. and is followed by said step of adding lignin sulfonate which comprises adding 100 parts 30% formaldehyde and condensing for 2.5 hours at 105° C., wherein an additional step of distilling off 40 parts water followed by cooling and diluting of the mass then takes place, followed by said step of adding lignin sulfonate wherein 200-300 parts 45% lignin sulfonate is then added, followed by stirring for 30 minutes at 30°-80° C., thereafter said step of adding urea and formaldehyde is effected by adding 20-50 parts urea, followed by stirring for 30 minutes at 30°-80° C. and thereafter adding 50-100 parts 30% formaldehyde, followed by stirring for 30 minutes at 30°-80° C., and wherein said step of adding sodium sulfite comprises adding 30-60 parts sodium sulfite followed by stirring for 30 minutes at 30°-80° C., and wherein said process additionally includes the step of adding water until a substance of desired dryness is obtained, and adjusting the pH to 4-8.

15. The process according to claim 11, wherein said sulfonating step comprises sulfonating 100 parts phenol with 120 parts conc. sulfuric acid for two hours at 115° C. in an autoclave followed by cooling to 50° C. and is followed by said condensing step which comprises condensing with 30 parts urea and 70-80 parts water for two hours at 50° C., subsequently adding 100 parts 30% formaldehyde and continuing the condensation for 12 hours at 30°-50° C., wherein said after-sulfonating step thereafter takes place and comprises heating up to 80° C. and after-sulfitizing with 30-60 parts sodium sulfite, wherein said step of adding lignin sulfonate then takes place and comprises adding 400-800 parts 45% lignin sulfonate and stirring for 60 minutes at 50°-80° C., wherein said step of adding formaldehyde thereafter takes place and comprises adding 100-300 parts 30% formaldehyde and stirring for 60 minutes at 50°-80° C., wherein said step of adding urea then takes place and comprises adding 20-50 parts urea and stirring for 60 minutes at 50°-80° C., and wherein said process additionally includes the steps of adding water until a substance of desired dryness is obtained and adjusting the pH to 4-8.

* * * * *